United States Patent
Kuroda et al.

(10) Patent No.: US 8,394,602 B2
(45) Date of Patent: Mar. 12, 2013

(54) LUMINESCENT METHOD FOR MEASURING ENDOTOXIN

(75) Inventors: Akio Kuroda, Higashihiroshima (JP); Kenichi Noda, Higashihiroshima (JP)

(73) Assignee: Hiroshima University, Hiroshima (JP)

( * ) Notice: Subject to any disclaimer, the term of this patent is extended or adjusted under 35 U.S.C. 154(b) by 252 days.

(21) Appl. No.: 12/734,485

(22) PCT Filed: Nov. 11, 2008

(86) PCT No.: PCT/JP2008/070450
§ 371 (c)(1),
(2), (4) Date: Jun. 28, 2010

(87) PCT Pub. No.: WO2009/063840
PCT Pub. Date: May 22, 2009

(65) Prior Publication Data
US 2011/0111441 A1      May 12, 2011

(30) Foreign Application Priority Data
Nov. 12, 2007   (JP) .................................. 2007-293491

(51) Int. Cl.
*C12Q 1/56*      (2006.01)
(52) U.S. Cl. ............................................ 435/13; 435/23
(58) Field of Classification Search .................... 435/13, 435/18, 23
See application file for complete search history.

(56) References Cited

U.S. PATENT DOCUMENTS
5,316,911 A    5/1994   Baek et al.
2009/0305353 A1   12/2009   Fujii et al.

FOREIGN PATENT DOCUMENTS
JP    2007-97577       4/2007
WO   WO 88/09507   * 12/1988
WO   99/15676          4/1999
WO   03/066611         8/2003

OTHER PUBLICATIONS

Fujii H. et al. Increase in Bioluminescence Intensity of Firefly Luciferase Using Genetic Modification. Analytical Biochemistry 366:131-136, 2007.*
Romaschin A. et al. A Rapid Assay of Endotoxin in Whole Blood Using Autologous Neutrophil Dependent Chemiluminescence J of Immunological Methods 212(2)169-185, Mar. 15, 1998.*
English Translation of the International Preliminary Report on Patentability.
International Search Report issued Jan. 6, 2009 in International (PCT) Application No. PCT/JP2008/070450.
European Office Action issued Dec. 3, 2010 in counterpart European Application No. EP 08 84 9709.
Lin Chen, "Reckoning Recombinant Factor", Pharmaceutical Formulation & Quality, Dec. 1, 2006, pp. 1-4, XP-002610023.
The Japanese Pharmacopoeia 15th Edition, The Ministry of Health, Labour and Welfare, Tokyo, Japan Chapter 4.01 Bacterial Endotoxins Tests, pp. 70-73, 2006 (English Translation).

* cited by examiner

*Primary Examiner* — Ralph Gitomer
(74) *Attorney, Agent, or Firm* — Wenderoth, Lind & Ponack, L.L.P.

(57) ABSTRACT

The present invention provides a method comprising allowing a reaction of a sample, a reagent containing Factor C, which can be activated by binding with endotoxin, and a synthetic luminescent substrate comprising a luminescent substrate bound to a peptide, for release of the luminescent substrate from the synthetic luminescent substrate, allowing a luminescent enzyme to act on the luminescent substrate released in the luminescent substrate release step, for measurement of the luminescence intensity, and quantifying the level of endotoxin in the sample based on a measured value obtained in the luminescence measuring step, the method enabling endotoxin to be simply and quickly measured at a level that cannot be detected in conventional methods for endotoxin measurement, without use of any dedicated measuring device.

9 Claims, 3 Drawing Sheets

LUMINESCENT METHOD FOR MEASURING ENDOTOXIN

This application is a U.S. national stage of International Application No. PCT/JP2008/070450 filed Nov. 11, 2008 which claims benefit of priority to Japan application 2007-293491 filed Nov. 12, 2007.

TECHNICAL FIELD

The present invention relates to a method and a kit for measurement of endotoxin level in a sample, and in particular relates to a method and a kit for measurement of endotoxin level using a bioluminescent reaction.

BACKGROUND ART

"Endotoxin" is a component of the cell wall in the outer membrane of gram-negative bacteria, and its activity is mainly attributed to LPS (lipopolysaccharide). In the living body, endotoxin exists as a part of the outer membrane in the surface layer of gram negative bacteria. Generally, after death of gram-negative bacteria, endotoxin is liberated and is present in a free form in blood.

When more than a certain level of endotoxin is present in blood, the endotoxin stimulates monocytes, granulocytes, etc., resulting in excessive production of inflammatory cytokines. Consequently, so called endotoxinemia accompanied by symptoms such as fever, sepsis, septic shock, multiple organ failure, etc. is induced. For this reason, detection of endotoxin in pharmaceuticals for injection, etc. is crucial, and thus the bacterial endotoxin test is prescribed by the Japanese, U.S. and European pharmacopeias. From the aspect of clinical diagnosis, precise measurement of blood endotoxin level is considered crucial for early diagnosis and therapeutic effect evaluation.

Examples of a conventional method for measuring endotoxin include the pyrogen test, in which a rabbit is treated with a direct injection of a test sample and measured for increase in body temperature that can be converted into the endotoxin level, and the Limulus test utilizing gelation of horseshoe crab amebocyte lysate triggered by endotoxin. The method involving direct injection into a rabbit has problems in cost, length of time required to obtain the test results, and sensitivity, and for this reason, the Limulus test currently prevails as a method for measuring endotoxin.

Figure 1:
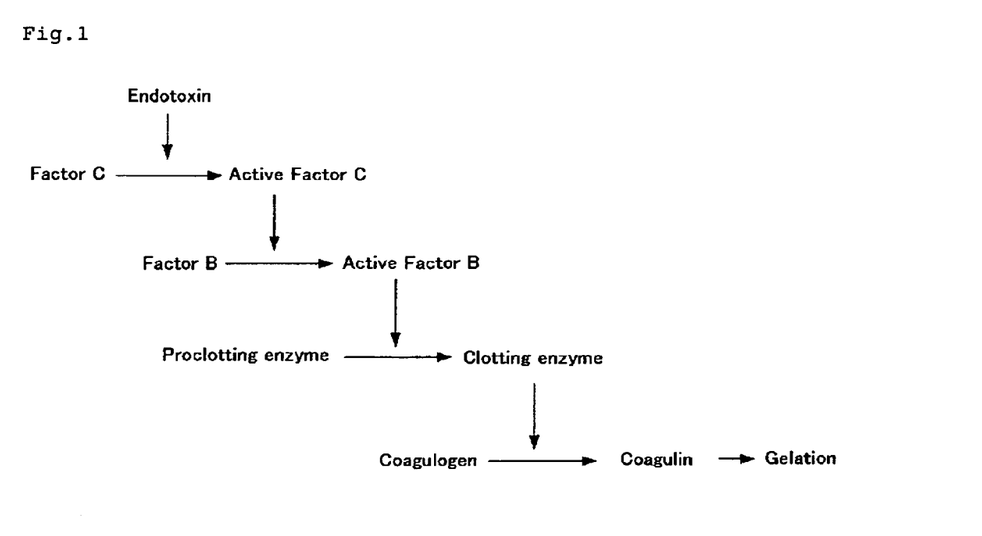
FIG. 1 shows a gelation process of horseshoe crab amebocyte lysate triggered by endotoxin.

A gelation process of horseshoe crab amebocyte lysate triggered by endotoxin is shown in FIG. 1. The gelation process of horseshoe crab amebocyte lysate contains a Factor C pathway specifically associated with endotoxin. The "Factor C pathway" is constituted by the following cascades. First, endotoxin firmly binds with Factor C, and thereby activates the Factor C. Then, Factor C activated by binding with endotoxin (active Factor C) activates Factor B. Subsequently, activated Factor B (active Factor B) activates a proclotting enzyme, resulting in production of a clotting enzyme. This clotting enzyme partially hydrolyzes its substrate, i.e., coagulogen. As a result, peptide C is liberated from the coagulogen, and a clotting protein, coagulin, is produced. By a coagulation action of the coagulin, gelation occurs (see nonpatent literature 1).

The Limulus test for measuring endotoxin utilizes the above-mentioned gelation process of horseshoe crab amebocyte lysate triggered by endotoxin. As the Limulus test, a gel-clot technique, a colorimetric technique using synthetic chromogenic substrates, a kinetic turbidimetric technique and the like are known and they are different in the ways of evaluation and measurement (see nonpatent literature 2).

"The gel-clot technique" is a method involving mixing horseshoe crab amebocyte lysate with a test sample in a test tube,
allowing the mixture to react under certain conditions (for example, 37° C. for 30 to 60 minutes),
inverting or tilting the test tube, and then
evaluating the test sample based on whether the mixture remains liquid or is solidified.

The test sample is evaluated as endotoxin negative in the former case, and as endotoxin positive in the latter case. This technique can be performed in a relatively easy manner without need of any special device. The technique, however, has problems in that difference of the material and production lots easily affects the test results, and in that the results are less objective as compared with optical methods because the way of evaluation relies on human eye observation. Therefore, the technique is usually used just as a quick test.

In the "colorimetric technique using synthetic chromogenic substrates," a synthetic chromogenic peptide substrate is used as a substrate of the clotting enzyme. The technique involves calculating an endotoxin level from absorbance of the amount of a released chromophore by colorimetric quantification. The synthetic chromogenic peptide substrate to be used has an amino acid sequence similar to that of the clotting enzyme-mediated hydrolysis site of a natural substrate coagulogen. The cleavage site (hydrolysis site) is bound to a chromophore, such as para-nitroaniline (pNA), and when the clotting enzyme cleaves off this chromophore, the free chromophore causes color formation. When the chromophore is para-nitroaniline, the absorbance at 405 nm, which is the maximal absorption wavelength of para-nitroaniline, is measured with time. When the chromophore is a diazotized para-nitroaniline, the absorbance at 545 nm is measured with time. After that, the resulting change with time in transmitted light amount is analyzed to determine the endotoxin level. The colorimetric technique using synthetic chromogenic substrates has problems, for example, in that reagents are relatively expensive, and in that the procedures are complicated, but is excellent in quantitative reliability, sensitivity and objectivity.

In the "kinetic turbidimetric technique," increase in turbidity caused by gelation is observed as change in transmitted light amount, and the elapsed time required for the transmitted light through the reaction mixture to decrease in ratio to a given threshold (usually about 90%) is regarded as a gelation time. The technique involves calculating an endotoxin level by use of a standard curve obtained by plotting the gelation time against the endotoxin level. This technique is extremely excellent in quantitative reliability and objectivity, but needs a dedicated device for measurement.

A reagent kit that enables highly sensitive measurement of endotoxin using a recombinant Factor C and a fluorescent substrate (trade name: PyroGene rFc, manufacturer: Lonza Walkersville, Inc., distributor: Daiichi Pure Chemicals Co., Ltd.) is commercially available.

Non Patent Literature

NPL 1:
T. Miyata, M. Hiranaga et al., Amino Acid Sequence of the Coagulogen from Limulus polyphemus Hemocytes, The Journal of Biological Chemistry, 259, 8924-8933 (1984)

NPL 2:
The Japanese Pharmacopoeia 15$^{th}$ Edition, The Ministry of Health, Labour and Welfare, Tokyo, Japan, Chapter 4.01 Bacterial Endotoxins Tests, pp. 70-73, 2006.

SUMMARY OF INVENTION

Problem to be Solved by the Invention

As described above, the Limulus test, such as a colorimetric technique using synthetic chromogenic substrates and a kinetic turbidimetric technique, is excellent in quantitative reliability and objectivity as a method for measuring endotoxin. However, it is pointed out that even with these techniques, there are still various problems in measuring endotoxin. For example, the test results do not always correspond to clinical symptoms. Specifically, even though infusions or dialysis fluids which have been evaluated as negative in the Limulus test are used, symptoms presumably caused by endotoxin, such as fever, often manifest. In some cases, even though a person is clinically diagnosed with severe gram negative bacterial infection, which may develop when blood has been infected with gram negative bacteria, the blood endotoxin level of the person is not evaluated as positive in the Limulus test. Behind these phenomena is a sensitivity problem that the conventional Limulus test still has.

For this reason, the development of a method for more highly sensitive measurement of endotoxin is a pressing need. As such a method, a simple method requiring no dedicated measuring device has been desired to be developed.

The present invention has been made in light of the above-mentioned problems, and an object thereof is to provide a method which enables endotoxin to be simply and quickly measured at a level that cannot be detected in conventional methods for endotoxin measurement, without use of any dedicated measuring device.

Means for Solving the Problem

The present inventors have conducted intensive studies to achieve the above-mentioned object. As a result, they have found that, by applying a bioluminescent reaction to the conventional Limulus test, endotoxin in a sample can be measured in a quick, simple and highly sensitive manner. Based on this finding, the present invention has been completed.

Namely, the present invention relates to a method for measurement of endotoxin level in a sample, comprising a luminescent substrate release step allowing a reaction of a sample, a reagent containing Factor C, which can be activated by binding with endotoxin, and a synthetic luminescent substrate comprising a luminescent substrate bound to a peptide, for release of the luminescent substrate from the synthetic luminescent substrate,
a luminescence measuring step allowing a luminescent enzyme to act on the luminescent substrate released in the luminescent substrate release step, for measurement of the luminescence intensity, and
a level determination step involving quantifying the level of endotoxin in the sample based on a measured value obtained in the luminescence measuring step.

Preferably, the synthetic luminescent substrate has such a structure that the bond of the luminescent substrate with the peptide is to be cleaved by the action of any one of active Factor C, active Factor B and a coagulating enzyme, each of which is produced by activating the Factor C. It is preferable that the luminescent substrate is aminoluciferin, and that the luminescent enzyme is luciferase.

Preferably, the luciferase is derived from a member of the order Coleoptera selected from the group consisting of a North American firefly, a Genji firefly, a Heike firefly, a glow worm, a Hime firefly, a Mado firefly, an Oba firefly, a Brazilian larval click beetle and a railroad worm. Further, the luciferase is preferably a mutant luciferase having a modified amino acid sequence of a wild type luciferase for an increased luminescence intensity as compared with that of the wild type luciferase.

The mutant luciferase is preferably one kind selected from the group consisting of the following (i) to (v):
(i) a mutant firefly luciferase comprising an amino acid sequence having substitutions of leucine for isoleucine at position 423, and of glycine for aspartic acid at position 436 as compared to the amino acid sequence of the wild type North American firefly luciferase represented by SEQ ID NO: 13;
(ii) a mutant firefly luciferase comprising an amino acid sequence having substitutions of leucine for isoleucine at position 423, and of arginine for leucine at position 530 as compared to the amino acid sequence of the wild type North American firefly luciferase represented by SEQ ID NO: 13;
(iii) a mutant firefly luciferase comprising an amino acid sequence having substitutions of glycine for aspartic acid at position 436 and of arginine for leucine at position 530 as compared to the amino acid sequence of the wild type North American firefly luciferase represented by SEQ ID NO: 13;
(iv) a mutant firefly luciferase comprising an amino acid sequence having substitutions of leucine for isoleucine at position 423, of glycine for aspartic acid at position 436, and of arginine for leucine at position 530 as compared to the amino acid sequence of the wild type North American firefly luciferase represented by SEQ ID NO: 13; and
(v) a mutant firefly luciferase comprising an amino acid sequence having substitutions of threonine for isoleucine at position 47, of serine for asparagine at position 50, of threonine for methionine at position 59, of serine for threonine at position 252, of leucine for isoleucine at position 423, and of arginine for leucine at position 530 as compared to the amino acid sequence of the wild type North American firefly luciferase represented by SEQ ID NO: 13.

It is preferable that the reagent containing Factor C is horseshoe crab amebocyte lysate, and that protein derived from the horseshoe crab amebocyte lysate is present at a concentration of 1.5 to 3.5 mg/mL relative to the whole volume of the reaction system.

According to the present invention, the kit for measurement of endotoxin level comprises, as components, a reagent containing Factor C, which can be activated by a specific binding with endotoxin, a synthetic luminescent substrate comprising a luminescent substrate bound to a peptide, and a luminescent enzyme.

Effect of the Invention

According to the method of the present invention, a bioluminescent reaction is applied to the measurement of endotoxin level and the endotoxin level is quantified based on luminescence emitted via the reaction. Therefore, without use of any dedicated measuring device, endotoxin can be simply and quickly measured at a level that cannot be detected in conventional methods for endotoxin measurement.

BEST MODE FOR CARRYING OUT THE INVENTION

1. Method for Measurement of Endotoxin Level

Firstly, the mechanism of the method for measurement of endotoxin level will be illustrated by reference to FIGS. 1 and 2. FIG. 1 shows a gelation process of horseshoe crab amebocyte lysate triggered by endotoxin, and FIG. 2 shows an exemplary method for measurement of endotoxin level according to the present invention.

As shown in FIG. 1, endotoxin firmly binds with Factor C and thereby activates the Factor C, and then activated Factor C (active Factor C) activates Factor B. Next, activated Factor B (active Factor B) activates a proclotting enzyme and thereby a clotting enzyme is produced. The clotting enzyme partially hydrolyzes a substrate called coagulogen, and thereby a clotting protein called coagulin is produced.

Figure 2:
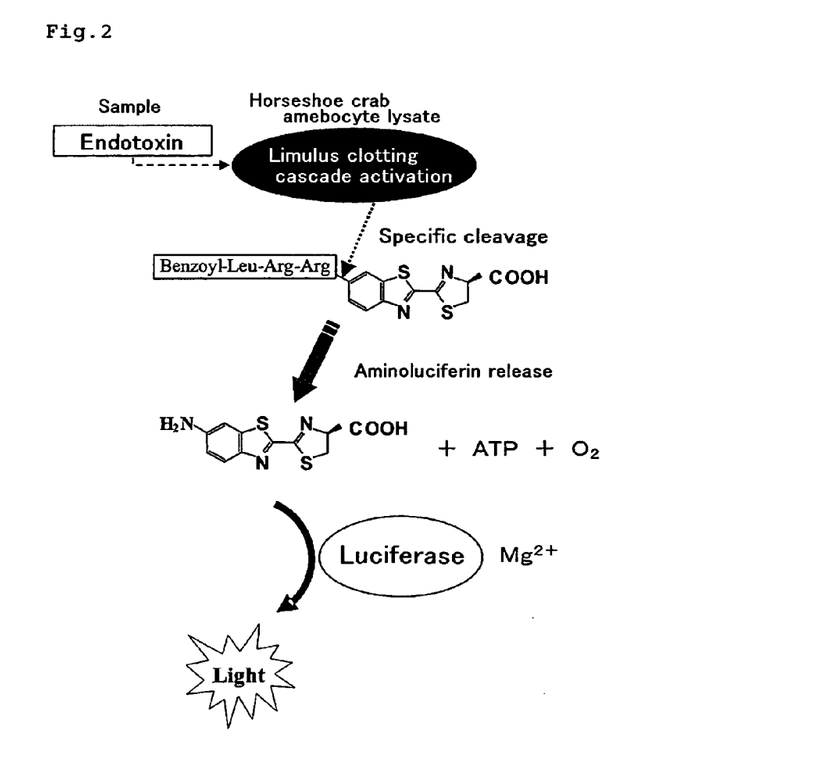
FIG. 2 shows an exemplary method for measurement of endotoxin level according to the present invention.

As shown in FIG. 2, when an endotoxin-containing sample has been brought into contact with horseshoe crab amebocyte lysate, endotoxin in the sample triggers activation of the limulus clotting cascade. Then, by addition of "benzoyl-Leu-Arg-Arg-aminoluciferin" as a substrate of the clotting enzyme to the reaction system, the clotting enzyme produced by the activation of the limulus clotting cascade, cleaves the bond of Arg and aminoluciferin, resulting in release of a luminescent substrate aminoluciferin. Luciferase (luminescent enzyme) is allowed to act on the aminoluciferin, resulting in light emission. The luciferin/luciferase luminescent reaction is shown in the following reaction formula (I).

(I)

According to the present invention, the method for measurement of endotoxin level comprises measuring luminescence emitted via the above-mentioned mechanism, and quantifying the level of endotoxin in the sample based on a measured value (luminescence).

Secondly, the method for measurement of endotoxin level will be illustrated in detail. According to the present invention, the method for measurement of endotoxin level comprises (1) a luminescent substrate release step allowing a reaction of a sample, a reagent containing Factor C, which can be activated by binding with endotoxin, and a synthetic luminescent substrate comprising a luminescent substrate bound to a peptide, for release of the luminescent substrate from the synthetic luminescent substrate, (2) a luminescence measuring step allowing a luminescent enzyme to act on the luminescent substrate released in the luminescent substrate release step, for measurement of the luminescence intensity, and (3) a level determination step involving quantifying the level of endotoxin in the sample based on a measured value obtained in the luminescence measuring step.

(1) Luminescent Substrate Release Step

The luminescent substrate release step allows a reaction of a sample, a reagent containing Factor C, which can be activated by binding with endotoxin (hereinafter referred to as a Factor C-containing reagent), and a synthetic luminescent substrate comprising a luminescent substrate bound to a peptide, for release of the luminescent substrate from the synthetic luminescent substrate.

[Sample]

The sample is not particularly limited, and examples thereof include pharmaceuticals such as injections, infusions and dialysis fluids, and clinical specimens such as blood (plasma) and urine. In the case where clinical specimens require inactivation of interference factors (inhibitors and promoting factors) participating in the limulus clotting cascade, the specimens should be subjected to pretreatment by a known inactivation method (for example, treatment with perchloric acid (the PCA method), the New PCA method, etc.).

[Factor C-Containing Reagent]

A suitable Factor C-containing reagent may be a horseshoe crab amebocyte lysate conventionally used for the Limulus test. Such a horseshoe crab amebocyte lysate is not particularly limited as long as it is derived from, for example, hemocytes of horseshoe crabs belonging to the Limulus sp., the *Tachypleus* sp. or the *Carcinoscorpius* sp., and it can produce the clotting enzyme via a reaction with endotoxin. Therefore, a commercially available Limulus reagent (LAL reagent), or a Limulus reagent (LAL reagent) provided in a kit for endotoxin measurement can be suitably used.

It is also possible to use a recombinant Factor C derived from a recombinant gene prepared based on all or a part of the horseshoe crab Factor C gene. A suitable example of the recombinant Factor C may be the recombinant Factor C provided in the commercially available PyroGene rFc (manufactured by Lonza Walkersville and Inc., distributed by Daiichi Pure Chemicals Co., Ltd.). Alternatively, the recombinant Factor C may be obtained by preparing an expression vector having the horseshoe crab Factor C gene inserted thereinto according to a known genetic engineering method, introducing the vector into appropriate host cells to achieve expression of a recombinant protein, and purifying the protein.

When the horseshoe crab amebocyte lysate conventionally used in the Limulus test (for example, a commercially available Limulus reagent) is used as the Factor C-containing reagent, the lysate reacts with an endotoxin-containing sample, resulting in production of active Factor C, active Factor B and a clotting enzyme. These proteins are known to have a protease activity. Therefore, in this case, a synthetic luminescent substrate having a recognition sequence for active Factor C, a synthetic luminescent substrate having a recognition sequence for active Factor B and a synthetic luminescent substrate having a recognition sequence for the clotting enzyme may be used. However, according to the present invention, since the method for measurement of endotoxin level uses, as an index, the protease activity of any one of active Factor C, active Factor B and the clotting enzyme, one of the above synthetic luminescent substrates corresponding to the selected enzyme is used.

Meanwhile, when the recombinant Factor C is used as the Factor C-containing reagent, the recombinant Factor C reacts with an endotoxin-containing sample, resulting in production of active recombinant Factor C only. This is because in this case, the Factor C-containing reagent contains neither Factor B nor the proclotting enzyme. Therefore, a synthetic luminescent substrate having a recognition sequence for active Factor C can be used.

When the horseshoe crab amebocyte lysate conventionally used in the Limulus test (for example, a commercially available Limulus reagent) is used as the Factor C-containing reagent, the amount thereof is preferably about 40% to 80% of the conventional amount thereof. This is because it was found that the conventional amount thereof (100%) inhibits the luminescent reaction and thereby provides a decreased luminescence intensity, but that about 40% to 80% of the conventional amount thereof provides a higher luminescence intensity. About 40% to 80% of the conventional amount thereof is equivalent to 1.5 to 3.5 mg/mL as a concentration of protein derived from horseshoe crab amebocyte lysate relative to the whole volume of the measurement system. More preferably, the protein concentration is 2.0 to 3.3 mg/mL. According to the present invention, since endotoxin can be measured in a highly sensitive manner by use of a less amount of the Factor C-containing reagent than the conventional amount thereof, the method for measurement of endotoxin level is extremely useful in industrial application.

[Synthetic Luminescent Substrate]

The synthetic luminescent substrate comprises a luminescent substrate bound to a peptide. The "luminescent substrate" as used herein refers to a light-emitting substance serving as a substrate in a bioluminescent reaction. A suitable luminescent substrate may be luciferin. Inter alia, especially preferred is aminoluciferin represented by the following formula (II). This is because an amide bond can be formed between the amino group of aminoluciferin and a carboxyl group of the adjacent amino acid.

(II)

The peptide, which is used for binding with aminoluciferin, comprises such an amino acid sequence that an amide bond to be formed with aminoluciferin in the C terminus can be cleaved by the protease activity of any one of active Factor C, active Factor B and the clotting enzyme. As long as this requirement is met, the number of amino acid residues and the amino acid sequence are not limited, but the number of amino acid residues is preferably 2 to 10 in terms of specificity, production cost, easy handling, etc.

Specific examples of the peptide having a recognition sequence for the clotting enzyme include Gly-Val-Ile-Gly-Arg- (SEQ ID NO: 1), Val-Leu-Gly-Arg- (SEQ ID NO: 2), Leu-Arg-Arg- (SEQ ID NO: 3), Ile-Glu-Gly-Arg- (SEQ ID NO: 4), Leu-Gly-Arg- (SEQ ID NO: 5), Val-Ser-Gly-Arg- (SEQ ID NO: 6) and Val-Gly-Arg- (SEQ ID NO: 7).

Specific examples of the peptide having a recognition sequence for the active Factor C include Ile-Glu-Ala-Arg- (SEQ ID NO: 8), Leu-Gly-Asn-Lys-Val-Ser-Arg- (SEQ ID NO: 9) and Ile-Thr-Thr-Val-Gly-Arg- (SEQ ID NO: 10).

Specific examples of the peptide having a recognition sequence for the active Factor B include Thr-Thr-Thr-Thr-Arg- (SEQ ID NO: 11) and Ser-Arg-Gln-Arg-Arg- (SEQ ID NO: 12).

The N terminus of the peptide may be protected by a protecting group. Any protecting group that is usually used in the technical field can be used without limitation. Specific examples thereof include an N-succinyl group, a tert-butoxycarbonyl group, a benzoyl group and a p-toluenesulfonyl group.

The synthetic luminescent substrate as used herein can be synthesized in reference to, for example, the method of Examples 6 and 7 of JP-W 2005-530485 (WO2003/066611). Alternatively, the synthetic luminescent substrate provided in "Proteasome-Glo™ Assay Systems" commercially available from Promega (benzoyl-Leu-Arg-Arg-aminoluciferin) can be used. When the synthetic luminescent substrate contains any free aminoluciferin, such aminoluciferin is preferably removed in advance. This is because the removal of the free aminoluciferin can reduce background luminescence. An exemplary method of removing the free aminoluciferin may be a method involving mixing the synthetic luminescent substrate with a solution containing 0.8 mM coenzyme A, 1.5 mM ATP, 250 µg/ml firefly luciferase and 90 mM DTT, in a buffer solution (pH 7.8) containing 20 mM tricine, 8 mM $Mg^{2+}$ and 0.13 mM EDTA, and then incubating the mixture at room temperature (25° C.) for 1 to 6 hours.

[Procedure (Method) for Reaction]

The procedure (method) for reaction of the sample, the Factor C-containing reagent and the synthetic luminescent substrate is not particularly limited, as long as the procedure is suitable for requirements for release of the luminescent substrate (aminoluciferin) from the synthetic luminescent substrate by reaction of the above three. An exemplary procedure may be a method involving mixing a sample and a Factor C-containing reagent well, incubating the mixture at 37° C. for about 5 to 60 minutes, adding a synthetic luminescent substrate thereto and then mixing well, and incubating the mixture at 37° C. for about 1 to 30 minutes.

(2) Luminescence Measuring Step

A luminescence measuring step allows a luminescent enzyme to act on the luminescent substrate released in the above luminescent substrate release step, for measurement of the luminescence intensity.

[Luminescent Enzyme]

The luminescent enzyme as used herein is any substance that catalyzes a bioluminescent reaction of the luminescent substrate released from the synthetic luminescent substrate, resulting in light emission. When the luminescent substrate is luciferin, luciferase is suitably used as the luminescent enzyme. When the luminescent substrate is aminoluciferin represented by the above-mentioned formula (II), a luciferase derived from a member of the order Coleoptera is used as the luminescent enzyme. As the luciferase derived from a member of the order Coleoptera, luciferases of a North American firefly, a Genji firefly, a Heike firefly, a glow worm, a Hime firefly, a Mado firefly, an Oba firefly, a Brazilian larval click beetle and a railroad worm can be suitably used. As for these luciferases derived from the Coleoptera, the amino acid sequence and the base sequence of the gene encoding the same are registered with the accession number shown in Table 1 in a known database (for example, EMBL Nucleotide Sequence Database (http://www.ebi.ac.uk/embl/)). The luciferase may be a native protein or a recombinant protein. The luciferase that can be used for the present invention is available as a commercial reagent from various companies.

TABLE 1

| Japanese name | Scientific name | Accession # |
| --- | --- | --- |
| North American firefly | *Photinus pyralis* | M15077 |
| Genji firefly | *Luciola cruciata* | M26194 |
| Heike firefly | *Luciola lateralis* | Z49891 |
| Glow worm | *Arachnocampa luminosa* | No data |
| Hime firefly | *Hotaria parvula* | L39929 |
| Mado firefly | *Pyrocoelia miyako* | L39928 |
| | *Pyrocoelia pygidialis* | EU826678 |
| | *Pyrocoelia pectoralis* | EF155570 |
| | *Pyrocoelia rufa* | AY447203 |
| Oba firefly | *Lucidina biplagiata* | No data |
| Brazilian larval click beetle | *Pyrearinus termitilluminans* | AF116843 |
| Railroad worm | *Phrixothrix vivianii* | AF139644 |
| | *Phrixothrix hirtus* | AF139645 |

The luciferase is not limited to a luciferase having a wild type amino acid sequence, and may be a mutant luciferase having a different amino acid sequence from the wild type amino acid sequence as long as it catalyzes a bioluminescence reaction of the luminescent substrate. Examples of the different amino acid sequence from the wild type amino acid sequence include an amino acid sequence having one or several amino acid deletions, insertions, substitutions or additions as compared to the wild type amino acid sequence. As used herein, "having one or several amino acid deletions, insertions, substitutions or additions" means that an amino acid(s) the number of which is practicable in a known method for preparing mutant polypeptides, such as site-directed mutagenesis (preferably 10 or less, more preferably 7 or less, and most preferably 5 or less), is(are) deleted, inserted, substituted or added.

As the mutant luciferase, preferred is a mutant luciferase having modification for an increased luminescence intensity because such a mutant luciferase enables highly sensitive measurement of an ultratrace level of endotoxin. Examples of the mutant luciferase having modification for an increased luminescence intensity include the following mutant luciferases.

(i) a mutant firefly luciferase comprising an amino acid sequence having substitutions of leucine (Leu) for isoleucine (Ile) at position 423, and of glycine (Gly) for aspartic acid (Asp) at position 436 as compared to the amino acid sequence of the wild type North American firefly luciferase (SEQ ID NO: 13);

(ii) a mutant firefly luciferase comprising an amino acid sequence having substitutions of leucine (Leu) for isoleucine (Ile) at position 423, and of arginine (Arg) for leucine (Leu) at position 530 as compared to the amino acid sequence of the wild type North American firefly luciferase;

(iii) a mutant firefly luciferase comprising an amino acid sequence having substitutions of glycine (Gly) for aspartic acid (Asp) at position 436 and of arginine (Arg) for leucine (Leu) at position 530 as compared to the amino acid sequence of the wild type North American firefly luciferase;

(iv) a mutant firefly luciferase comprising an amino acid sequence having substitutions of leucine (Leu) for isoleucine (Ile) at position 423, of glycine (Gly) for aspartic acid (Asp) at position 436, and of arginine (Arg) for leucine (Leu) at position 530 as compared to the amino acid sequence of the wild type North American firefly luciferase; and (v) a mutant firefly luciferase comprising an amino acid sequence having substitutions of leucine (Leu) for isoleucine (Ile) at position 423, of arginine (Arg) for leucine (Leu) at position 530, of threonine (Thr) for isoleucine (Ile) at position 47, of serine (Ser) for asparagine (Asn) at position 50, of threonine (Thr) for methionine (Met) at position 59, and of serine (Ser) for threonine (Thr) at position 252 as compared to the amino acid sequence of the wild type North American firefly luciferase.

It was confirmed that each of the above-mentioned mutant firefly luciferases (i) to (v) provides an increased luminescence intensity by (1) 18-fold, (ii) 18-fold, (iii) 8-fold, (iv) 20-fold and (v) 21-fold as compared with the North American firefly luciferase (wild type), respectively (see JP-A 2007-97577).

The above-mentioned mutant firefly luciferase can be prepared by modifying a wild type firefly luciferase gene, inserting the modified gene into an expression vector by a known method, introducing the vector into appropriate host cells to achieve expression of a recombinant protein, and purifying the protein. Exemplary methods for modifying genes include site-specific mutagenesis, random mutagenesis and organic synthesis, which are known by those skilled in the art. The base sequence of the North American firefly luciferase gene (cDNA) is registered with the accession number M15077 in a database (for example, EMBL Nucleotide Sequence Database (http://www.ebi.ac.uk/embl/)). The above-mentioned mutant firefly luciferases (i) to (v) can be prepared in reference to the Examples of JP-A 2007-97577.

Those skilled in the art can also easily prepare mutant luciferases of a Genji firefly, a Heike firefly, a Hime firefly, a Mado firefly, a Brazilian larval click beetle and a railroad worm, by a known method based on the base sequences of the respective wild type luciferase genes (see Table 1) registered in a known database. In reference to the amino acid substitution in the above-mentioned mutant firefly luciferases (i) to (v) derived from the North American firefly, those skilled in the art can easily prepare a mutant luciferase that provides an increased luminescence intensity by substitution of an amino acid(s) at the corresponding position(s)) in another Coleoptera luciferase.

[Procedure (Method) for Reaction and Measurement]

A luminescent enzyme (luciferase) is added to the reaction mixture obtained in the above luminescent substrate release step, i.e., the reaction mixture containing a released luminescent substrate (aminoluciferin). Since the luciferin/luciferase luminescent reaction requires ATP and a divalent metallic ion as shown in the above-mentioned reaction formula (I), it is preferable, for example, to dissolve luciferase in a buffer solution containing ATP and magnesium ion and then to add this luciferase solution to the above reaction mixture. Specifically, for example, the luciferase solution is added to start a reaction at room temperature (25° C.), and 2 to 10 seconds after the addition, the luminescence intensity is measured.

A commercially available luminometer (luminescence measuring device) can be used for measuring the luminescence intensity. There is no particular limitation on its manufacturer and performance, but preferred is a luminometer having a measurable relative luminescence intensity ranging from 0 to 10 million. Specifically, for example, Lumitester C1000 manufactured by KIKKOMAN CORP., and ARVO Light manufactured by PerkinElmer, Inc. are suitable in specifications. The luminescence measurement may be performed according to the attached manual of the device.

(3) Level Determination Step

The level determination step involves quantifying the level of endotoxin in the sample based on a measured value obtained in the luminescence measuring step. By use of endotoxin solutions of predetermined different concentrations, a standard curve that represents a relation between the predetermined endotoxin concentration and a luminescence value therefor is made. The endotoxin level in a test sample can be determined by applying a measured value for the test sample obtained in the above-mentioned luminescence measuring step to this standard curve.

2. Kit for Measurement of Endotoxin Level

According to the present invention, the kit for measurement of endotoxin level comprises a Factor C-containing reagent, a synthetic luminescent substrate and a luminescent enzyme as components. Since the details of the components are already illustrated above, the repetitive description is avoided here. There is no particular limitation on specific components other than the above components in the kit, and any reagent, equipment or other requirements for the kit may be appropriately selected and incorporated into the kit. By use of the kit of the present invention, the above-mentioned method for measurement of endotoxin level can be performed in a simple and quick manner.

The term "kit" as used herein is intended to be a package provided with containers (for example, bottles, plates, tubes, dishes, etc.) each holding a specific material. Preferably, the kit is provided with an instruction manual for using the aforementioned material. The instruction manual may be written or printed on paper or other media, or may be provided in the form of electronic media, such as magnetic tape, computer-readable disk or tape, and CD-ROM.

3. Examples

Hereinafter, the present invention will be illustrated in detail by way of examples, but is not limited thereto. The equipment, reagents, water, etc. used in the following examples were endotoxin free or, if not, contained such an ultratrace level of endotoxin as not to affect test results of endotoxin measurement.

Example 1

Endotoxin Measurement by Bioluminescence Method

<Methods>

The Limulus reagent (LAL), the endotoxin standard solution (*E. coli* 0111:B4 endotoxin), and the pyrogen free water all provided in the endotoxin measurement kit QCL-1000 (Lonza Walkersville, Inc.) were used. The synthetic luminescent substrate used in this example was benzoyl-Leu-Arg-Arg-aminoluciferin provided in Proteasome-Glo™ Assay Systems (Promega). The luciferase used in this example was a wild type North American firefly luciferase that the present inventors prepared by *E. coli* expression and purification. Specifically, the luciferase was prepared by excising the North American firefly luciferase (wild type) gene from the PicaGene cassette vector (manufactured by Toyo Ink), inserting the gene into the *E. coli* expression vector pET28a (Novagen), introducing the resulting expression vector into *E. coli* for expression of the desired luciferase, and purifying the luciferase.

First, the endotoxin standard solution was diluted with the pyrogen free water to prepare samples at 9 levels ranging from 0.0001 to 0.1 endotoxin unit (EU)/mL. The pyrogen free water containing no endotoxin was used as a blank. Next, 50 μL each of the samples and the blank was separately transferred to reaction test tubes each containing 50 μL of the Limulus reagent, and the mixture was mixed for several seconds with a vortex mixer. After mixing, the tubes were heated in an incubator at 37±1.0° C. for exact 10 minutes. The detailed operations were as described in the attached protocol of the QCL-1000.

Then, into each tube was added 50 μL of a 150 μM solution of the synthetic luminescent substrate (benzoyl-Leu-Arg-Arg-aminoluciferin) in 100 mM Tris-Cl (pH 8.0) supplemented with 1 mM $MgCl_2$, and the tubes were heated for exact 5 minutes in the incubator at 37±1.0° C. After heating, the reaction mixture was transferred to a test tube exclusively used for bioluminescence measurement (Lumitube manufactured by KIKKOMAN CORP.), and to this was added 50 μL of a solution of luciferase in 100 mM Tris-Cl (pH 8.0) supplemented with $10^{-5}$ M ATP and 1 mM $MgCl_2$. The tube was set into Lumitester C1000 (KIKKOMAN CORP.) to measure the luminescence intensity of the sample.

As Comparative Example, the colorimetric endpoint assay was performed for the same samples, using the chromogenic substrate provided in the QCL-1000 instead of the above-mentioned synthetic luminescent substrate. The operations were as described in the attached protocol of the QCL-1000.

<Results>

Figure 3:
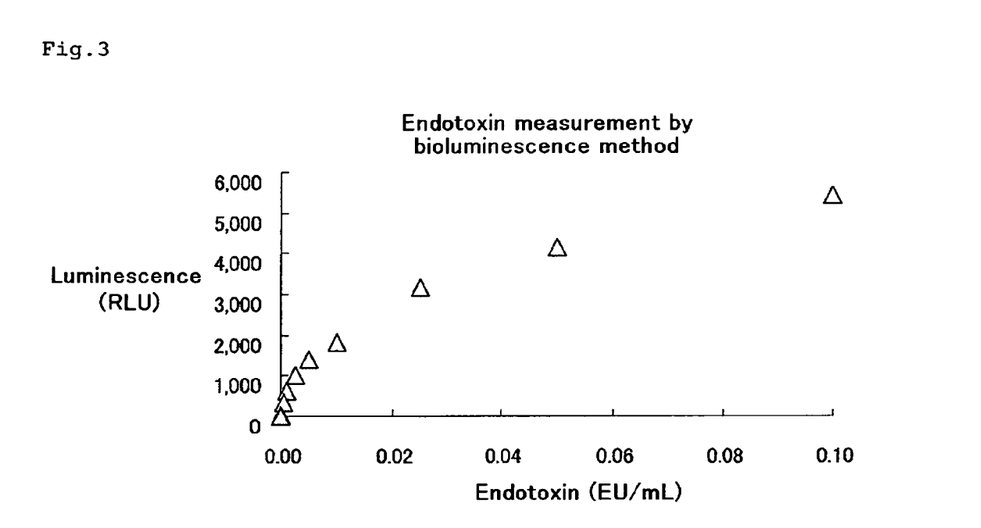
FIG. 3 is a graph of luminescence intensity plotted against the sample concentration in Example 1.
Figure 4:
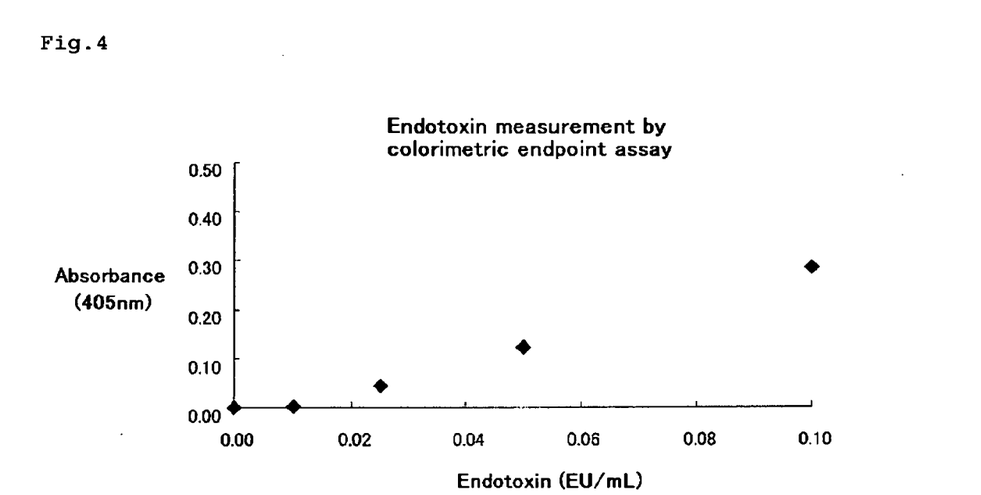
FIG. 4 is a graph of absorbance plotted against the sample concentration in Comparative Example.

The results of Example 1 are shown in FIG. 3. The results of Comparative Example are shown in FIG. 4. FIG. 3 is a graph of luminescence intensity plotted against the sample concentration in Example 1. FIG. 4 is a graph of absorbance plotted against the sample concentration in Comparative Example. As shown in FIG. 4, in the colorimetric endpoint assay using the conventional chromogenic substrate, the endotoxin levels of 0.025 EU/mL or less could not be quantitatively evaluated because of extremely low measured values. Meanwhile, as shown in FIG. 3, in the luminescence measurement using the synthetic luminescent substrate, the endotoxin levels of 0.01 EU/mL or less were measurable.

Figure 5:
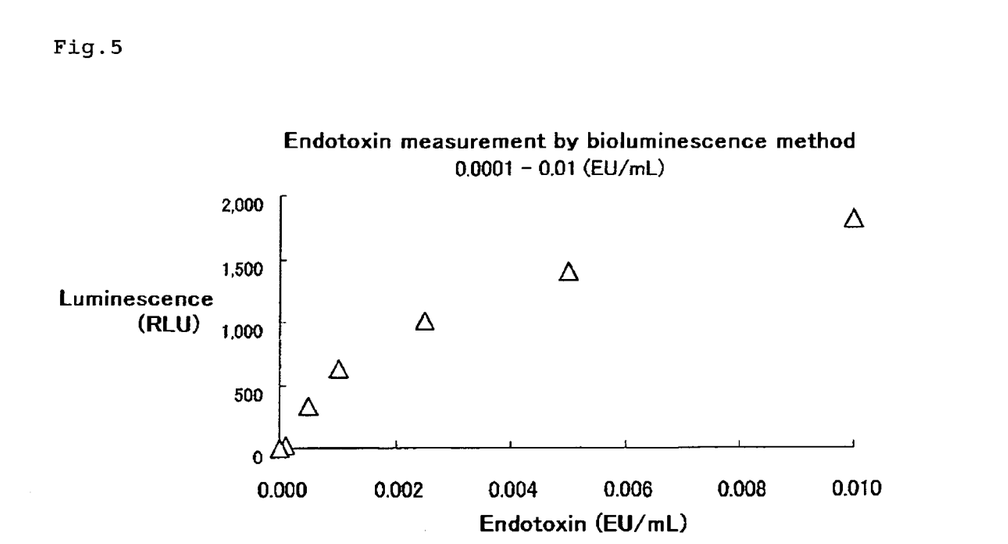
FIG. 5 is a detail graph of FIG. 3, showing luminescence intensity at the sample concentrations of 0.01 EU or less.

FIG. 5 is a detail graph of FIG. 3, showing luminescence intensity at the sample concentrations of 0.01 EU or less. As is clear from FIG. 5, in the bioluminescence measurement, the endotoxin level of 0.0005 EU/mL was measurable.

Example 2

Endotoxin Measurement by Bioluminescence Method Using Mutant Luciferase

In the method of the present invention for measurement of endotoxin level, a mutant luciferase that had been confirmed to provide a higher luminescence intensity than the wild type luciferase was used.

<Methods>

The mutant luciferase used in this example comprises an amino acid sequence having substitutions of leucine for isoleucine at position 423, of arginine for leucine at position 530, of threonine for isoleucine at position 47, of serine for asparagine at position 50, of threonine for methionine at position 59, and of serine for threonine at position 252 as compared to the amino acid sequence of the wild type North American firefly luciferase. This mutant luciferase was prepared by the present inventors according to the method of Example 14 in JP-A 2007-97577.

The endotoxin standard solution was diluted with the pyrogen free water in the same manner as in Example 1, to prepare samples at 12 levels ranging from 0.0001 to 1.0 EU/mL. The pyrogen free water containing no endotoxin was used as a blank. The procedures were the same as those of Example 1 except that both of the luciferase used in Example 1 (wild type luciferase), and the above-mentioned mutant luciferase were used. In this example, the colorimetric endpoint assay as a control was not performed.

<Results>

The results are shown in Table 2. As is clear from Table 2, the luminescence intensity at the endotoxin level of 0.0001 EU/mL was about 400 RLU, and this was 10-fold or more as compared with the intensity in the case of using the wild type luciferase. The results show that a trace level of endotoxin can be measured in a highly sensitive manner by use of the mutant luciferase. Considering the background value in the bioluminescence measurement was 20 to 30 RLU, the results suggest that endotoxin at an ultratrace level of 0.0001 EU/mL or less is also measurable by use of the mutant luciferase.

TABLE 2

| Endotoxin (EU/ml) | Wild-type (RLU) | Mutant (RLU) |
| --- | --- | --- |
| 1.0 | 14,539 | 72,343 |
| 0.50 | 11,216 | 63,190 |
| 0.25 | 8,539 | 53,723 |
| 0.10 | 5,452 | 43,042 |
| 0.05 | 4,156 | 35,242 |
| 0.025 | 3,176 | 29,823 |
| 0.01 | 1,815 | 21,785 |
| 0.005 | 1,404 | 17,230 |
| 0.0025 | 1,017 | 12,783 |
| 0.001 | 637 | 7,863 |
| 0.0005 | 333 | 3,563 |
| 0.0001 | 23 | 428 |
| 0 | 0 | 0 |

Example 3

Endotoxin Measurement by Bioluminescence Method Using Wild Type and Mutant Luciferases The endotoxin level was measured by use of the same materials and methods as in Example 2. In Example 2, numerical values obtained after subtraction of the blank value are shown as a measured value (see Table 2), whereas in Example 3, actual measured values without blank subtraction are shown as a measured value.

The results are shown in Table 3. As is clear from Table 3, the detection limit in the measurement using the wild type luciferase was 0.005 EU/mL, whereas in the measurement using the mutant luciferase, the endotoxin level of as low as 0.0005 EU/mL was measurable. Like the results of Example 2, the results of Example 3 also show that a trace level of endotoxin can be measured in a highly sensitive manner by use of the mutant luciferase. In the case of using the mutant luciferase, the luminescence intensity at the endotoxin level of 0.0001 EU/mL was about 5,500 RLU, and this was 10-fold or more as compared with the intensity in the case of using the wild type luciferase. Considering the background value in the bioluminescence measurement was 20 to 30 RLU, the results suggest that endotoxin at an ultratrace level of 0.0001 EU/mL or less is also measurable by use of the mutant luciferase.

TABLE 3

| Endotoxin (EU/ml) | Wild-type (RLU) | Mutant (RLU) |
| --- | --- | --- |
| 1.00 | 4,374 | 87,474 |
| 0.50 | 4,066 | 81,321 |
| 0.25 | 3,643 | 78,854 |
| 0.10 | 3,259 | 73,173 |
| 0.05 | 2,519 | 50,373 |
| 0.025 | 2,048 | 44,954 |
| 0.010 | 1,618 | 36,916 |
| 0.005 | 1,050 | 32,361 |
| 0.0025 | 635 | 27,914 |
| 0.0010 | 583 | 20,994 |
| 0.0005 | 550 | 12,694 |
| 0.0001 | 524 | 5,560 |
| 0 | 504 | 5,131 |

Example 4

Examination of Effects of Limulus Reagent (LAL) Concentration on Luminescence Intensity <Methods>

The endotoxin standard solution was diluted with the pyrogen free water to prepare a sample of 0.05 endotoxin unit (EU)/mL. To the Limulus reagent (LAL) was added the pyrogen free water to prepare 9 levels of diluted LALs at concentrations ranging 90% (LAL:water=9:1) to 10% (LAL:water=1:9). In addition to these, an undiluted Limulus reagent (100%) and a solution containing no Limulus reagent (LAL) (0%: pyrogen free water only), namely 11 levels of Limulus reagents (LALs), were used for the test.

The luciferase used in this example was the mutant luciferase used in Examples 2 and 3, and the other reagents used in this example were the same as those used in Example 1. The assay procedures were the same as those of Example 1. The whole volume of each measurement system was 200 μL containing 50 μL of the sample, 50 μL of a different level Limulus reagent (LAL), 50 μL of the synthetic luminescent substrate solution, and 50 μL of the luciferase solution. The 11 levels of Limulus reagents (LALs) were measured for protein concentration by absorption spectroscopy at a wavelength of 280 nm ($OD_{280}$=1 means a protein concentration of 1 mg/mL).

Figure 6:
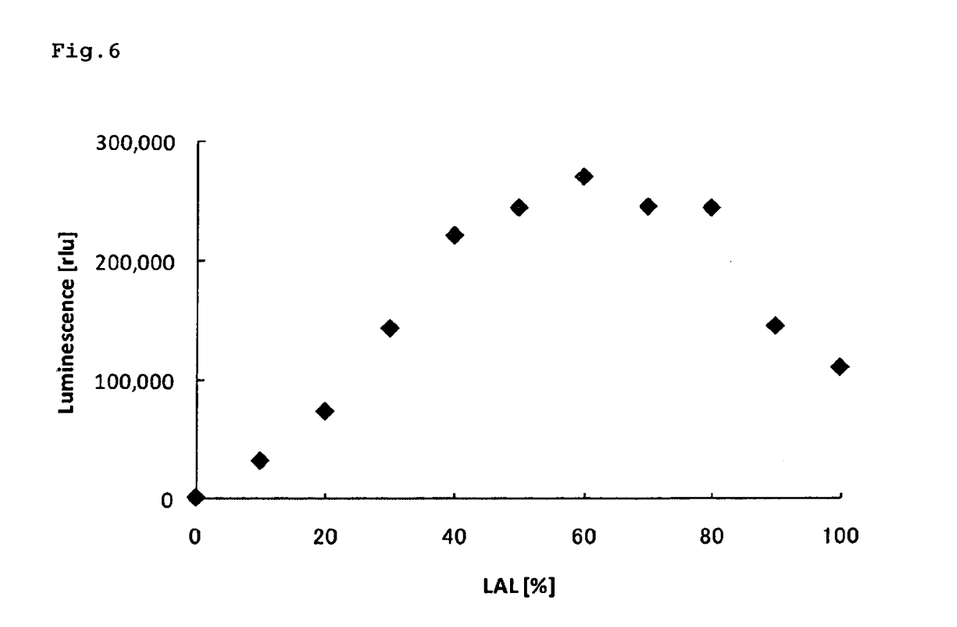
FIG. 6 is a graph of luminescence intensity plotted against the Limulus reagent concentration in Example 4.

The results are shown in Table 4 and FIG. 6. The LAL concentration in Table 4 represents the final concentration of LAL in the measurement system (200 μL). As is clear from Table 4 and FIG. 6, the use of 100% LAL (undiluted) and 90% LAL inhibited the luminescent reaction and thereby provided a decreased luminescence intensity, i.e., a decreased sensitivity. Meanwhile, it was found that the use of 40 to 80% LALs provided a higher luminescence intensity. This range of the LAL concentration was equivalent to the range of 1.67 to 3.33 mg/mL in terms of the LAL-derived protein concentration relative to the whole volume of the measurement system. The results show that endotoxin can be measured in a highly sensitive manner by use of a less amount of LAL than the conventional amount for ordinary use.

TABLE 4

| LAL [%] | LAL conc. [mg/mL] | Luminescence [rlu] |
| --- | --- | --- |
| 0 | 0.00 | 2,246 |
| 10 | 0.42 | 33,173 |
| 20 | 0.83 | 74,927 |
| 30 | 1.25 | 144,917 |
| 40 | 1.67 | 222,307 |
| 50 | 2.08 | 245,338 |
| 60 | 2.50 | 271,338 |
| 70 | 2.91 | 246,471 |
| 80 | 3.33 | 245,448 |
| 90 | 3.74 | 147,131 |
| 100 | 4.16 | 112,394 |

As described above, according to the present invention, it is possible to measure the endotoxin level of 0.0005 EU/mL in an endpoint assay. This level is lower than the minimum detection limit (0.025 EU/mL) in the colorimetric endpoint assay, which is one of the conventional Limulus tests that can be performed within the same measurement period as that of the present invention. It was also shown that in the method of the present invention, the measurement can be completed within 15 minutes unlike the kinetic turbidimetric technique, which can detect the endotoxin level of 0.001 EU/mL and requires 180 minutes or more for measurement. Further, it was suggested that by use of a mutant luciferase that provides a higher luminescence intensity than the wild type luciferase, endotoxin at an ultratrace level of 0.0001 EU/mL or less is also measurable. Furthermore, it was shown that by use of a less amount of the Limulus reagent (LAL), i.e., 0.4- to 0.8-fold volume (final concentration: 1.5 to 3.5 mg/mL) as compared with the conventional volume thereof, the luminescence intensity is increased and thereby endotoxin can be measured in a highly sensitive manner.

From these results, the use of the present invention can prevent side effects caused by contamination of the pharmaceuticals for injection, etc. by endotoxin at a level that cannot be detected in conventional methods. Since the present invention enables measurement of an ultratrace level of endotoxin in clinical samples, the relation of various symptoms and endotoxin levels in a living body can be clarified. The present invention also enables early diagnosis and early treatment of endotoxinemia, and thereby is expected to bring a great contribution to the clinical setting. Furthermore, highly sensitive reagents for endotoxin measurement can be provided at low cost.

The present invention is not limited to the aforementioned embodiments and examples, and various modifications can be made within the scope of the appended claims. Other embodiments provided by appropriately combining different technical means disclosed in each embodiment of the present invention are also within the technical scope of the present invention. All the academic publications and patent literatures cited in the above description are incorporated herein by reference.

INDUSTRIAL APPLICABILITY

The present invention can be used in the medical field, especially the pharmaceutical manufacturing field and the clinical examination field.

The invention claimed is:

1. A method for measurement of an endotoxin level in a sample, comprising:

reacting sample, a reagent, and a synthetic luminescent substrate, wherein the reagent contains Factor C, optionally Factor B and optionally a coagulating enzyme, wherein the synthetic luminescent substrate comprises a luminescent substrate bound to a peptide, wherein endotoxin present in the sample binds to the Factor C to form activated Factor C, wherein the activated Factor C binds to the Factor B if present to form activated Factor B, wherein the activated Factor B if present binds to the coagulating enzyme if present to form activated coagulating enzyme, wherein the bond between the luminescent substrate and the peptide of the synthetic luminescent substrate is cleaved by any one of the activated Factor C, the activated Factor B or the activated coagulating enzyme to release the luminescent substrate from the synthetic luminescent substrate, reacting a luminescent enzyme with the released luminescent substrate to generate luminescence, measuring the luminescence intensity, and quantifying the level of endotoxin in the sample based on the measured luminescent intensity.

2. The method according to claim 1, wherein the luminescent substrate is aminoluciferin and the luminescent enzyme is luciferase.

3. The method according to claim 2, wherein the luciferase is derived from a member of the order Coleoptera selected from the group consisting of a North American firefly, a Genji firefly, a Heike firefly, a glow worm, a Hime firefly, a Mado firefly, an Oba firefly, a Brazilian larval click beetle and a railroad worm.

4. The method according to claim 2, wherein the luciferase is a mutant luciferase having a modified amino acid sequence of a wild type luciferase for an increased luminescence intensity as compared with that of the wild type luciferase.

5. The method according to claim 4, wherein the mutant luciferase is selected from the group consisting of following (i) to (v):
  (i) a mutant firefly luciferase comprising an amino acid sequence having substitutions of leucine for isoleucine at position 423, and of glycine for aspartic acid at position 436 as compared to the amino acid sequence of the wild type North American firefly luciferase represented by SEQ ID NO: 13;
  (ii) a mutant firefly luciferase comprising an amino acid sequence having substitutions of leucine for isoleucine at position 423, and of arginine for leucine at position 530 as compared to the amino acid sequence of the wild type North American firefly luciferase represented by SEQ ID NO: 13;
  (iii) a mutant firefly luciferase comprising an amino acid sequence having substitutions of glycine for aspartic acid at position 436 and of arginine for leucine at position 530 as compared to the amino acid sequence of the wild type North American firefly luciferase represented by SEQ ID NO: 13;
  (iv) a mutant firefly luciferase comprising an amino acid sequence having substitutions of leucine for isoleucine at position 423, of glycine for aspartic acid at position 436, and of arginine for leucine at position 530 as compared to the amino acid sequence of the wild type North American firefly luciferase represented by SEQ ID NO: 13; and
  (v) a mutant firefly luciferase comprising an amino acid sequence having substitutions of threonine for isoleucine at position 47, of serine for asparagine at position 50, of threonine for methionine at position 59, of serine for threonine at position 252, of leucine for isoleucine at position 423, and of arginine for leucine at position 530 as compared to the amino acid sequence of the wild type North American firefly luciferase represented by SEQ ID NO: 13.

6. The method according to claim 1, wherein the reagent containing Factor C is horseshoe crab amebocyte lysate, and protein derived from the horseshoe crab amebocyte lysate is present at a concentration of 1.5 to 3.5 mg/mL relative to the whole volume of the reaction system.

7. The method according to claim 1, wherein the measurement can be completed within 15 minutes.

8. The method according to claim 1, wherein the level of endotoxin in a sample is measurable at an ultratrace level of 0.0001 EU/mL.

9. The method according to claim 1, wherein the LAL-derived protein concentration relative to the whole volume of the measurement system is the range of 1.5 to 3.5 mg/mL.

* * * * *

```
                            SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Synthetic construct; peptide

<400> SEQUENCE: 1

Gly Val Ile Gly Arg
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic construct; peptide

<400> SEQUENCE: 2

Val Leu Gly Arg
1

<210> SEQ ID NO 3
<211> LENGTH: 3
<212> TYPE: PRT
<213> ORGANISM: Artificial Sequence
<220> FEATURE:
<223> OTHER INFORMATION: Synthetic construct; peptide

<400> SEQUENCE: 3

Leu Arg Arg
1

<210> SEQ ID NO 4
<211> LENGTH: 4
<212> TYPE: PRT
<213> ORGANISM: Artificial Sequence
<220> FEATURE:
```

<223> OTHER INFORMATION: Synthetic construct; peptide

<400> SEQUENCE: 4

Ile Glu Gly Arg
1

<210> SEQ ID NO 5
<211> LENGTH: 3
<212> TYPE: PRT
<213> ORGANISM: Artificial Sequence
<220> FEATURE:
<223> OTHER INFORMATION: Synthetic construct; peptide

<400> SEQUENCE: 5

Leu Gly Arg
1

<210> SEQ ID NO 6
<211> LENGTH: 4
<212> TYPE: PRT
<213> ORGANISM: Artificial Sequence
<220> FEATURE:
<223> OTHER INFORMATION: Synthetic construct; peptide

<400> SEQUENCE: 6

Val Ser Gly Arg
1

<210> SEQ ID NO 7
<211> LENGTH: 3
<212> TYPE: PRT
<213> ORGANISM: Artificial Sequence
<220> FEATURE:
<223> OTHER INFORMATION: Synthetic construct; peptide

<400> SEQUENCE: 7

Val Gly Arg
1

<210> SEQ ID NO 8
<211> LENGTH: 4
<212> TYPE: PRT
<213> ORGANISM: Artificial Sequence
<220> FEATURE:
<223> OTHER INFORMATION: Synthetic construct; peptide

<400> SEQUENCE: 8

Ile Glu Ala Arg
1

<210> SEQ ID NO 9
<211> LENGTH: 7
<212> TYPE: PRT
<213> ORGANISM: Artificial Sequence
<220> FEATURE:
<223> OTHER INFORMATION: Synthetic construct; peptide

<400> SEQUENCE: 9

Leu Gly Asn Lys Val Ser Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic construct; peptide -continued

```
<400> SEQUENCE: 10

Ile Thr Thr Val Gly Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic construct; peptide

<400> SEQUENCE: 11

Thr Thr Thr Thr Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic construct; peptide

<400> SEQUENCE: 12

Ser Arg Gln Arg Arg
1               5

<210> SEQ ID NO 13
<211> LENGTH: 550
<212> TYPE: PRT
<213> ORGANISM: Photinus pyralis

<400> SEQUENCE: 13

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220
```

-continued

```
Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550
```